United States Patent
Makuuchi et al.

Patent Number: 5,846,214
Date of Patent: Dec. 8, 1998

[54] PVA HYDROGEL, HYDROGEL LAMINATE USING THE SAME AND HYDROGEL WOUND-DRESSING MATERIAL USING THE SAME

[75] Inventors: Keizo Makuuchi, Gunma-ken; Fumio Yoshii, Takasaki; Yasuaki Kitazaki, Iruma; Kotohiko Shinozaki, Sayama; Kazuki Isobe, Iruma; Yuko Nishisako, Omiya, all of Japan

[73] Assignees: Nichiban Company Limited; Japan Atomic Energy Research Institute, both of Tokyo, Japan

[21] Appl. No.: 824,564

[22] Filed: Mar. 26, 1997

[30] Foreign Application Priority Data

| Mar. 29, 1996 | [JP] | Japan | 8-077592 |
| Mar. 29, 1996 | [JP] | Japan | 8-077631 |
| Mar. 29, 1996 | [JP] | Japan | 8-077923 |

[51] Int. Cl.⁶ .................................................... A61F 13/00
[52] U.S. Cl. ............................................................ 602/52
[58] Field of Search ........................ 602/41, 48–52, 602/54, 56, 58, 900, 904; 604/368; 424/445; 514/777.2, 944

[56] References Cited

U.S. PATENT DOCUMENTS

| 3,957,605 | 5/1976 | Assarsson et al. | 604/368 |
| 4,524,064 | 6/1985 | Nambu | 602/900 |
| 4,750,482 | 6/1988 | Sieverding | 128/156 |
| 5,037,409 | 8/1991 | Chen et al. | 604/358 |
| 5,106,876 | 4/1992 | Kawamura | 522/5 |
| 5,115,801 | 5/1992 | Cartmell et al. | 602/48 |
| 5,143,071 | 9/1992 | Keusch et al. | 128/640 |
| 5,219,325 | 6/1993 | Hennick et al. | 602/58 |
| 5,393,798 | 2/1995 | Weber | 521/149 |
| 5,465,735 | 11/1995 | Patel | 128/888 |
| 5,480,717 | 1/1996 | Kundel | 602/56 |
| 5,489,262 | 2/1996 | Cartmell et al. | 602/57 |

FOREIGN PATENT DOCUMENTS

| 0610056 | 8/1994 | European Pat. Off. | 602/52 |
| WO 94/12134 | 6/1994 | WIPO | 602/52 |
| WO 94/13235 | 6/1994 | WIPO | 602/52 |

*Primary Examiner*—Manuel Mendez
*Attorney, Agent, or Firm*—Frishauf, Holtz, Goodman, Langer & Chick, P.C.

[57] ABSTRACT

Disclosed are a PVA hydrogel which comprises being obtained by irradiating a polyvinyl alcohol aqueous solution containing a polymer selected from the group consisting of polyvinyl pyrrolidone, a methyl vinyl ether-maleic anhydride copolymer and an isobutylene-maleic anhydride copolymer, with ionizing radiations, a process for preparing the PVA hydrogel, a hydrogel laminate using the PVA hydrogel, a process for preparing the hydrogel laminate, and a hydrogel wound-dressing material using the PVA hydrogel.

25 Claims, 1 Drawing Sheet

PVA HYDROGEL, HYDROGEL LAMINATE USING THE SAME AND HYDROGEL WOUND-DRESSING MATERIAL USING THE SAME

BACKGROUND OF THE INVENTION

1. Field of the Invention

This invention relates to a polyvinyl alcohol (hereinafter abbreviated to "PVA") hydrogel which is useful as a living body-compatible material, particularly a wound-dressing material, a laminate which comprises plural PVA hydrogel layers being laminated, and a PVA hydrogel wound-dressing material which is excellent in strength, water absorptivity and water retentivity, has adhesion and also is excellent in peelability.

2. Prior Art

A PVA hydrogel obtained by crosslinking a PVA aqueous solution by irradiation with ionizing radiation is transparent, has heat resistance and is excellent in chemical resistance, gas permeability and antibacterial property such that the PVA hydrogel has been expected to be a living body-compatible material for a wound-dressing material.

As a process for preparing such a hydrogel, as described in, for example, Japanese Provisional Patent Publication No. 358532/1992, there has been known a process in which a 10 to 40% PVA aqueous solution is irradiated with ionizing radiation, the aqueous solution is dried and then the dried solution is dipped in water to be swelled. Further, as a method for increasing the strength of the gel, in Medical Mechanics Vol. 62, pp. 285 to 289 (1992), there has been described a method of drying a PVA aqueous solution, subjecting the dried solution to heat treatment and irradiating the treated solution with ionizing radiation.

However, PVA hydrogels obtained by these methods lack compatibility with skin, i.e., flexibility, adhesivity, patching property. It was difficult to adjust these properties.

On the other hand, techniques for imparting adhesion to a hydrogel have been described in Japanese Patent Publication No. 66151/1993 and Japanese Provisional Patent Publication No. 230659/1989. According to these techniques, by adding a special additive such as cyclodextrin and a divalent metal salt, a hydrogel having adhesion can be obtained.

However, according to these techniques, the resulting PVA hydrogel has a problem that the additive remains. When the PVA hydrogel is provided for medical use, particularly used as a wound-dressing material or the like which is directly contacted with a skin, it has problems in stabilities of shape-maintaining property and adhesion against change in temperature and change with the lapse of time.

When the PVA hydrogel is used as, for example, a wound-dressing material, various changes in characteristics such as adjustment of the strength of the whole gel and control of a time when a medicine to be introduced into the gel is diffused in the gel are demanded depending on an application position and use. However, these changes cannot be dealt with easily by the conventional PVA hydrogel.

Further, in Japanese Patent Publication No. 77171/1991, there has been described a percutaneously absorptive preparation in which a pharmacologically active substance or a pharmacologically active substance, an absorption aid and/ or an adhesion-imparting material is/are contained in a PVA hydrogel.

However, in a wound-dressing material using the conventional PVA hydrogel, which results in problems in quality, use, process and so on, e.g., high cost, poor heat resistance and, low flexibility, low adhesivity to wounds on the face and skin.

SUMMARY OF THE INVENTION

The present inventors have found that by crosslinking a PVA aqueous solution containing PVA and a polymer selected from polyvinyl pyrrolidone (hereinafter abbreviated to "PVP"), a methyl vinyl ether-maleic anhydride copolymer (hereinafter abbreviated to "VEMA") and an isobutylene-maleic anhydride copolymer (hereinafter abbreviated to "IBMA") by irradiation with ionizing radiation, a PVA hydrogel, which may be adhesive, in which the above problems can be solved can be obtained without using a special additive. Also, they have found that since adhesion can be controlled not only by adjusting a formulation ratio and/or a concentration but also by adjusting an absorbed dose, adhesion can be easily controlled.

Also, the present inventors have found that the above problems can be solved by a laminate which comprises plural layers of the same or different PVA hydrogels as the above which may be adhesive.

Further, the present inventors have found that a hydrogel wound-dressing material which comprises the following constitutional materials being laminated in the following order:

(1) a support layer;
(2) a water-absorptive supporting layer comprising a PVA hydrogel; and
(3) a hydrogel layer comprising a PVA hydrogel which may be adhesive has excellent strength, water absorptivity and water retentivity, a base material is not softened even after absorbing an exudate, the hydrogen wound-dressing material can be peeled completely and easily, the base material does not remain after peeling, the hydrogel itself may have adhesion, and the hydrogen wound-dressing material has high usefulness in the aspects of practical use and hygiene.

DESCRIPTION OF THE PREFERRED EMBODIMENTS

Figure 1:
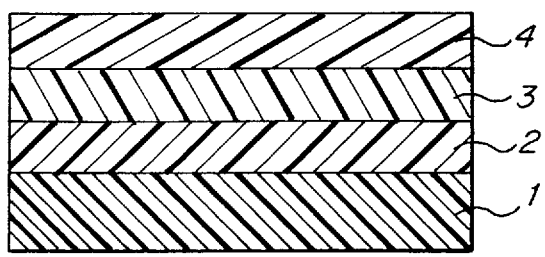
FIG. 1 is a hydrogel laminate prepared according to Example 4.

In the following, the present invention is explained in detail.

The PVA aqueous solution to be used for preparing the PVA hydrogel and the hydrogel laminate of the present invention is an aqueous solution which contains PVA as an essential component and further contains either of PVP, VEMA or IBMA, or a plurality of them.

PVA to be used is preferably PVA having a saponification degree of 78 to 100 mole % and an average polymerization degree of 1,000 or more, more preferably PVA having a saponification degree of 97 mole % or more and an average polymerization degree of 1,500 to 2,000. PVP to be used is preferably PVP having a weight average molecular weight of 20,000 to 1,500,000, more preferably PVP having a weight average molecular weight of 25,000 to 1,500,000, for example, of 25, 30 or 90 of K-value. VEMA is preferably VEMA having a weight average molecular weight of 200,000 to 900,000, more preferably VEMA having a weight average molecular weight of 800,000 or more. IBMA is preferably IBMA having a weight average molecular weight of 10,000 to 1,000,000, more preferably IBMA having a weight average molecular weight of 30,000 to 500,000.

In the PVA aqueous solution to be used for preparing the PVA hydrogel of the present invention, the contents of PVA, PVP, VEMA and IBMA are 5 to 90% by weight, 5 to 80% by weight, 5 to 70% by weight and 5 to 70% by weight based on the total weight of these polymers, respectively.

When PVP is contained in the PVA aqueous solution to be used for preparing the hydrogel laminate of the present invention, the formulation ratio (weight ratio) of PVA to PVP is preferably 2:8 to 8:2 from the point of imparting flexibility. Also, the formulation ratio (weight ratio) of PVA to PVP, VEMA and/or IBMA is preferably 1:9 to 9:1, more preferably 2:8 to 8:2 from the point of imparting adhesion.

The concentration of the PVA aqueous solution is preferably 5 to 50% by weight, more preferably 10 to 40% by weight in order to retain a certain amount of water after irradiation.

Flexibility can be imparted by incorporating a water-soluble plasticizer such as glycerin, polyglycerin, polyethylene glycol (PEG), polypropylene glycol (PPG) and Macrogol into the PVA aqueous solution.

If necessary, there may be contained a plasticizer other than the above plasticizers, for example, a polyvalent alcohol such as ethylene glycol (EG), diethylene glycol (DEG), propylene glycol (PG), dipropylene glycol (DPG) and an ethylene-propylene glycol copolymer; saccharides such as monosaccharides and polysaccharides.

In order to impart adhesion, polyacrylic acid, a sodium salt thereof, an ester thereof, cyclodextrin, gum arabic, pectin or the like may be added to the PVA aqueous solution.

Additionally, a humectant, a colorant and a pharmacologically active substance such as an antifungal agent, an anti-inflammatory agent and an anodyne may be added to the PVA aqueous solution. They may be added after irradiation. Further, if necessary, a water-soluble colorant having good compatibility with PVA may be formulated.

It is preferred that after the PVA aqueous solution is made to have a desired thickness by coating (flow casting) or injection molding (casting), or in a state that the solution is put in a bottle such as a glass container, the solution is irradiated with ionizing radiation so that the absorbed dose is 20 to 80 kGy.

The thickness of the coating film of the PVA aqueous solution is not particularly limited, but it is preferred to adjust the thickness depending on the permeation ability of ionizing radiations to be used.

Also, in order to obtain adhesion, the thickness is preferably 10 $\mu$m or more.

Ionizing radiations may include $\gamma$ ray, electron beam and X ray. Electron beam is particularly preferred from easiness of controlling the absorbed dose and irradiation depth.

The absorbed dose of ionizing radiations is preferably 20 to 100 kGy, more preferably 20 to 60 kGy. However, when a layer having a low crosslinking density is to be prepared, the absorbed dose may be 10 kGy or more.

The ionizing radiation is either of $\gamma$ ray, electron beam or X ray. However, the dose rate of electron beam is 500 times or more that of $\gamma$ ray such that a product can be prepared by irradiation in a short period of time. Therefore, successive production can be carried out. Thus, when the hydrogel is industrially produced on a large scale, it is desired to use an electron beam. Also, irradiation with an electron beam in a short period of time can be carried out, and deterioration of an object to be irradiated due to oxidation or the like is not caused such that it can be said that irradiation with electron beam is the preferred irradiation. The dose required for preparing the hydrogel may vary depending on the mixing ratio of PVA to other components, but a preferred dose is 20 to 80 kGy. If the dose is 10 kGy or less, crosslinking is insufficient such that sufficient strength cannot be obtained. If the dose is 90 kGy or more, crosslinking proceeds too much such that adhesion is lowered. Irradiation with a predetermined dose for obtaining the hydrogel may be carried out by one irradiation at a high dose rate, or may be carried out by batchwise irradiation in which several irradiations with divided doses are carried out.

Irradiation with a $\gamma$ ray has high permeation ability and therefore is advantageous for obtaining a thick hydrogel. The dose of the $\gamma$ ray may be the same as that of electron beam.

The hydrogel laminate according to the present invention may be obtained by a process which comprises one or more steps of coating the PVA aqueous solution on a PVA hydrogel layer which has already been formed, followed by irradiating the PVA aqueous solution with ionizing radiation. For example, the hydrogel laminate according to the present invention is obtained by repeating the steps of further coating the PVA aqueous solution on a PVA hydrogel layer which has already been formed, and irradiating the PVA aqueous solution with ionizing radiation. The hydrogel laminate may have three or more hydrogel layers.

Here, in all of the hydrogel layers, PVA aqueous solutions which are different in either of components, a formulation ratio, a concentration or the like or all of them may be used. In some of the hydrogel layers, the same PVA aqueous solution may be used, or in all of the hydrogel layers, the same PVA aqueous solution may be used.

The absorbed doses of ionizing radiation may be the same in all of the formed hydrogel layers, or the absorbed doses of the ionizing radiation may be different in all of the formed hydrogel layers, or the absorbed doses of ionizing radiation may be the same in plural optional layers of the formed hydrogel layers.

By changing the exposed dose and the thickness of coating, a PVA hydrogel laminate in which the layers have different crosslinking degrees and different thicknesses may be prepared. As the exposed dose is heightened, the crosslinking degree is heightened, whereby a PVA hydrogel having higher strength can be obtained.

Various non-woven fabrics, films, nets or the like may be sandwiched between the respective layers depending on the case, or a support layer of various non-woven fabrics, films, foams, nets or the like may be provided. The non-woven fabric or film or the like to be used between the layers is preferably a PVA non-woven fabric, a PVA film, a polypropylene non-woven fabric or a polyolefin net such as a polyethylene net or a polypropylene net, for example, DEL-NET which is available from AET (USA). The film or foam or the like to be used as a support is a polyurethane film, a polyurethane foam, a PVA non-woven fabric, a PVA film, a polypropylene (PP) non-woven fabric, a polyurethane non-woven fabric, a polyolefin net such as a polyethylene net or a polypropylene net or a composite support comprising a polyurethane film or a polyurethane foam and a PVA non-woven fabric, a PVA film or a PP non-woven fabric.

The hydrogel layer of the hydrogel wound-dressing material according to the present invention may be prepared by using the same starting material and the same method as in the PVA hydrogel and the hydrogel laminate described above.

However, in the PVA aqueous solution to be used for preparing a hydrogel layer of the hydrogel wound-dressing material of the present invention, the respective formulation amounts are preferably 10 to 100% by weight of PVA, 20 to 80% by weight of PVP and 0 to 70% by weight of VEMA or IBMA.

The hydrogel layer thus obtained has flexibility and gives mild adhesion to a wound portion to facilitate application. At the time of peeling, the hydrogel layer can be peeled completely and easily, and a base material does not remain at the wound portion after peeling. Further, the hydrogel layer itself has water absorptivity and is useful for absorbing an exudate.

The water-absorptive supporting layer comprises the same or similar components as in the hydrogel layer and can be prepared preferably by coating an aqueous solution containing 10 to 100% by weight of PVA and 0 to 90% by weight of PVP and immediately carrying out treatment with ionizing radiations. Flexibility can be also imparted to the water-absorptive supporting layer by incorporating a plasticizer thereinto similarly as in the hydrogel layer, such as glycerin, polyglycerin and polyethylene glycol. Also, a pharmacologically active substance such as an antifungal agent, an anti-inflammatory agent and an anodyne may be incorporated into the water-absorptive supporting layer similarly as in the hydrogel layer. Both of the hydrogel layer and the water-absorptive supporting layer have inherent characteristics and advantages as the PVA hydrogel. Therefore, both of the layers may be laminated and irradiated with ionizing radiation to be integrated with crosslinking, whereby hydrogel layers forming one matrix as a whole are obtained.

The water-absorptive supporting layer has functions of improving property of absorbing an exudate and protecting a wound portion from external stimulation due to the cushion property of the hydrogel.

The intermediate layer is a layer which is not essential, but improves anchoring and integration of the hydrogel layer and the support layer. Particularly when a hydrophobic adhesive, for example, an acryl adhesive is laminated between the support and the intermediate layers, the hydrophobic adhesive and the hydrophilic hydrogel can be integrated.

As the material to be used for the intermediate layer, various non-woven fabrics, films or nets (e.g., polyethylene net such as DELNET) may be used. However, from the points of compatibility with the hydrogel layer and transparency, a non-woven fabric of polypropylene or PVA, a PVA film or polyolefin net is preferred, and a PVA non-woven fabric is preferred also from the point of flexibility.

In the support layer, various non-woven fabrics, films and nets having flexibility and moisture permeability may be used. However, from the points of retaining wet circumstances suitable for healing of a wound and obtaining a cushion property and protectivity of a wound portion, a polyurethane film and a polyurethane foam are preferred.

The support layer has functions of fixing the hydrogel to a wound portion and protecting the wound portion from external stimulation, and is also useful for retaining the dressing material in a wet state suitable for healing a wound.

The PVA hydrogel of the present invention does not contain a crosslinking agent such that said hydrogel is extremely safe for a human body. Further, only by changing the exposed dose, adhesion can be easily controlled.

The PVA hydrogel laminate of the present invention can deal with changes in strength, flexibility and a releasing rate of a medicine extremely easily depending on use and an application position.

Further, the wound-dressing material of the present invention is excellent in compatibility with a living body, has a property of absorbing an exudate and a property of protecting a wound portion and can maintain wet circumstances suitable for healing a wound. The PVA hydrogel is excellent in morphological stability, there is no contamination of a wound portion which is observed in a wound-dressing material using hydrocolloid as a base material. Therefore, the wound-dressing material of the present invention is a wound-dressing material having desirable effects in the aspects of hygiene and use.

EXAMPLES

The present invention is described in detail by referring to the following Examples.

EXAMPLE 1

80 g of an aqueous solution containing 20% by weight of PVA having a saponification degree of 98.5% and a polymerization degree of 1700 was mixed with 20 g of an aqueous solution containing 20% by weight of PVP having a weight average molecular weight of 40,000 to obtain a PVA aqueous solution.

Next, on a polyethylene terephthalate (PET) film support, the obtained PVA-mixed aqueous solution was coated to have a thickness of 250 $\mu$m. The coating surface was irradiated with 40 kGy of an electron beam at one time to form a PVA hydrogel on the polyester film.

EXAMPLE 2

A PVA hydrogel was formed by the same procedures as in Example 1 except for using a mixed solution of 50 g of an aqueous solution containing 20% by weight of PVA having a saponification degree of 98.5% and a polymerization degree of 1700 and 50 g of an aqueous solution containing 20% by weight of PVP having a weight average molecular weight of 40,000 in place of the PVA aqueous solution of Example 1.

EXAMPLE 3

A PVA hydrogel was formed by the same procedures as in Example 1 except for using a mixed solution of 60 g of an aqueous solution containing 20% by weight of PVA having a saponification degree of 98.5% and a polymerization degree of 1700, 20 g of an aqueous solution containing 20% by weight of PVP having a weight average molecular weight of 40,000 and 20 g of an aqueous solution containing 20% by weight of VEMA having a weight average molecular weight of 900,000 in place of the PVA aqueous solution of Example 1.

As a comparative sample, a PVA hydrogel was formed by the same procedures as in Example 1 except for using an aqueous solution containing 20% by weight of PVA having a saponification degree of 98.5% and a polymerization degree of 1700.

Under conditions of 23° C. and a relative humidity of 65%, the smooth surface of the tip end of a metal rod having a diameter of 5 mm was contacted with each surface of the PVA hydrogels with a load of 100 g for 1 second, and a resistance value (a probe tack value) when the metal rod was drawn apart at a rate of 10 mm per second was measured (see ASTM No. 360). The results are shown in Table 1.

TABLE 1

|  | Probe tack value (N/5 mm φ) |
|---|---|
| Example 1 | 1.48 |
| Example 2 | 1.82 |
| Example 3 | 1.09 |
| Comparative sample | 0.56 |

EXAMPLE 4

Step 1: Preparations of Various PVA Aqueous Solutions 20 g of PVA having a saponification degree of 98.5% and a polymerization degree of 1700 and 80 g of water were taken in a glass conical flask of 300 cc and heated for 20 minutes by using an autoclave at 121° C. to dissolve PVA, whereby a first PVA aqueous solution was prepared. Also, an aqueous solution containing 20% by weight of VEMA having a weight average molecular weight of 900,000 was prepared. 40 g of the VEMA aqueous solution and 40 g of the first PVA aqueous solution were taken in a glass conical flask of 300 cc and mixed to prepare a second PVA aqueous solution containing PVA and VEMA.

Step 2: Preparation of a Hydrogel Laminate

As shown in FIG. 1, on a polyurethane film support 1, the first PVA aqueous solution was coated to have a thickness of 250 μm, and the coating surface was irradiated from an upper side with 20 kGy of an electron beam at one time to form a first hydrogel layer 2 on the polyurethane film. Next, the first PVA aqueous solution was further coated on the first hydrogel layer 2 to have a thickness of 250 μm, and the coating surface was irradiated from an upper side with an electron beam the exposed dose of which was raised to 40 kGy to form a second hydrogel layer 3 on the first hydrogel layer 2. Similarly, the second PVA aqueous solution was coated on the second hydrogel layer 3 to have a thickness of 250 μm, and the coating surface was irradiated from an upper side with 60 kGy of an electron beam at one time to form a third hydrogel layer 4 on the second hydrogel layer 3. In the resulting laminate, the layers are firmly bonded and physically integrated.

EXAMPLE 5

On a polyurethane film (a support layer) on which an acrylic adhesive was laminated, a PVA non-woven fabric (an intermediate layer) was superposed to form a base material.

On the base material, an aqueous solution containing 16% of PVA and 4% of glycerin was coated to have a thickness of about 300 μm by a film applicator. The coating film was irradiated with 40 kGy of an electron beam to form an water-absorptive supporting layer.

On the water-absorptive supporting layer, a solution obtained by mixing a 20% PVA aqueous solution and a 20% VEMA aqueous solution at a ratio of 8:2 was coated to have a thickness of 250 μm. The coating film was irradiated with 40 kGy of an electron beam to form a hydrogel layer (PVA+VEMA layer) having a thickness of 250 μm.

After a PET film was laminated on the hydrogel layer by using the surface of said layer as a peeling liner, the resulting material was punched out to prepare a wound-dressing material.

We claim:

1. A process for preparing a hydrogel laminate, which comprises:
coating a polyvinyl alcohol aqueous solution, said solution optionally comprises at least one polymer selected from the group consisting of polyvinyl pyrrolidone, a methyl vinyl ether-maleic anhydride copolymer and an isobutylene-maleic anhydride copolymer, to form at least one hydrogel layer, on a previously formed polyvinyl alcohol hydrogel layer, followed by irradiating the polyvinyl alcohol aqueous solution with ionizing radiation.

2. A hydrogel laminate produced by the process according to claim 1, which comprises a plurality of hydrogel layers formed by the same or different hydrogels.

3. The laminate according to claim 2, wherein the hydrogel layers are obtained from different polyvinyl alcohol aqueous solutions.

4. The laminate according to claim 2, wherein all of the hydrogel layers are obtained from the same polyvinyl alcohol aqueous solution.

5. The laminate according to claim 2, wherein some of the hydrogel layers are obtained from the same polyvinyl alcohol aqueous solution.

6. The laminate according to claim 2, wherein the absorbed doses of ionizing radiation are the same in all of the hydrogel layers.

7. The laminate according to claim 2, wherein the absorbed doses of ionizing radiation are different in all of the hydrogel layers.

8. The laminate according to claim 2, wherein the absorbed doses of ionizing radiation are the same in a plurality of layers among the layers.

9. The laminate according to claim 2, wherein at least one of said hydrogel layers is adhesive.

10. A hydrogel wound-dressing material comprising a hydrogel laminate produced by the process according to claim 1, which comprises the following layers being laminated in the following order:
(a) a support layer;
(b) a water-absorptive supporting layer comprising a polyvinyl alcohol hydrogel; and
(c) at least one of said hydrogel layers.

11. The material according to claim 10, wherein the water-absorptive supporting layer comprises a hydrogel which contains polyvinyl alcohol or polyvinyl alcohol and polyvinyl pyrrolidone and is obtained by irradiation with ionizing radiation.

12. The material according to claim 10, wherein at least one of the hydrogel layer and the water-absorptive supporting layer comprise at least one plasticizer selected from the group consisting of glycerin, polyglycerin and polyethylene glycol.

13. The material according to claim 10, wherein the support layer comprises a polyurethane film or a polyurethane foam.

14. The material according to claim 10, which further comprises an intermediate layer comprising a non-woven fabric, a film or a net intermediate layer, which is disposed between the water-absorptive supporting layer and the support layer.

15. The material according to claim 14, wherein the intermediate layer comprises a non-woven fabric of polypropylene or polyvinyl alcohol, a polyvinyl alcohol film, or polyolefin net.

16. The material according to claim 10, wherein at least one of said at least one hydrogel layers is adhesive.

17. The process according to claim 1, wherein the polyvinyl alcohol has a saponification degree of 78 to 100 mole %, and an average polymerization degree of 1,000 or more.

18. The process according to claim 17, wherein the polyvinyl alcohol has a saponification degree of 97 mole % or mole, and an average polymerization degree of 1,500 to 2,000; the polyvinyl alcohol aqueous solution comprising 5 to 90 weight % of the polyvinyl alcohol, 5 to 80 weight % of the polyvinyl pyrrolidone, 5 to 70 weight % of the methyl vinyl ether-maleic anhydride copolymer, and 5 to 70 weight % of the isobutylene-maleic anhydride copolymer, based on the total weight of the polymers.

19. The process according to claim 18, wherein the polyvinyl pyrrolidone has a weight average molecular weight of 20,000 to 1,500,000; the methyl vinyl ether-maleic anhydride copolymer has a weight average molecular weight of 200,000 to 900,000; and the isobutylene-maleic anhydride copolymer has a weight average molecular weight of 10,000 to 1,000,000.

20. The process according to claim 19, wherein the irradiating with the ionizing radiation is such that the polyvinyl alcohol aqueous solution receives an absorbed dose of the radiation of 20 to 80 kGy.

21. The process according to claim 20, wherein the coating of the polyvinyl alcohol aqueous solution forms a thickness of 10 $\mu$m or more.

22. The process according to claim 1, wherein at least one hydrogel layer is adhesive.

23. The process according to claim 1, wherein the hydrogel laminate has at least three hydrogel layers.

24. The process according to claim 1, wherein said at least one hydrogel layer comprises a plurality of hydrogel layers, wherein in all of said hydrogel layers, said polyvinyl alcohol aqueous solutions with respect of at least one of components of said polyvinyl alcohol aqueous solutions, a formulation ratio of the polyvinyl alcohol to the polyvinyl pyrrolidone, and a concentration of said polyvinyl alcohol aqueous solutions, are different from each other; or some of said hydrogel layers comprise the same polyvinyl alcohol aqueous solution; or all of said hydrogel layers comprise the same polyvinyl alcohol aqueous solution.

25. A process for preparing a hydrogel laminate, which consists essentially of:
(a) coating a layer of a polyvinyl alcohol aqueous solution on a previously formed polyvinyl alcohol hydrogel layer, said polyvinyl alcohol aqueous solution optionally comprises at least one polymer selected from the group consisting of polyvinyl pyrrolidone, a methyl vinyl ether-maleic anhydride copolymer and an isobutylene-maleic anhydride copolymer,
(b) thereafter irradiating said polyvinyl alcohol aqueous solution with ionizing radiation, said layer of said polyvinyl alcohol aqueous solution having a thickness which is adjusted depending on the permeating ability of said ionizing radiation to crosslink said polyvinyl alcohol aqueous solution, to form said at least one hydrogel layer of said polyvinyl alcohol aqueous solution on said previously formed polyvinyl alcohol hydrogel layer.

* * * * *